(12) United States Patent
Sovereign et al.

(10) Patent No.: US 7,972,825 B2
(45) Date of Patent: Jul. 5, 2011

(54) INTEGRATED APPARATUS FOR ETHANOL PRODUCTION AND EXTRACTION

(75) Inventors: Scott Sovereign, Sparta, MI (US); Frank A. VanKempen, Coopersville, MI (US)

(73) Assignee: ENE003, LLC, Walker, MI (US)

( * ) Notice: Subject to any disclaimer, the term of this patent is extended or adjusted under 35 U.S.C. 154(b) by 258 days.

(21) Appl. No.: 12/370,721

(22) Filed: Feb. 13, 2009

(65) Prior Publication Data

US 2010/0209548 A1    Aug. 19, 2010

(51) Int. Cl.
| C12P 7/16 | (2006.01) |
| C12P 7/14 | (2006.01) |
| C12C 11/00 | (2006.01) |
| A21D 2/00 | (2006.01) |

(52) U.S. Cl. ...... 435/161; 435/162; 435/163; 435/291.1; 435/298.1; 426/11; 426/16; 426/18; 426/29

(58) Field of Classification Search ............... 426/2, 11, 426/16, 18, 29; 435/161, 162, 163, 291.1, 435/298.1
See application file for complete search history.

(56) References Cited

U.S. PATENT DOCUMENTS

| 1,860,554 A | 5/1932 | Ricard et al. |
| 3,201,155 A | 8/1965 | Billeter et al. |
| 3,871,272 A | 3/1975 | Melandri |
| 4,003,798 A | 1/1977 | McCord |
| 4,112,829 A | 9/1978 | Poinsard et al. |
| 4,278,502 A | 7/1981 | Stevens et al. |
| 4,305,790 A | 12/1981 | Kramer, Sr. |
| 4,306,023 A | 12/1981 | Crombie |
| 4,308,106 A | 12/1981 | Mannfeld |
| 4,336,335 A | 6/1982 | Muller et al. |
| 4,344,828 A | 8/1982 | Melton |
| 4,372,822 A | 2/1983 | Muller et al. |
| 4,376,109 A * | 3/1983 | Wolter et al. ............... 423/659 |
| 4,460,687 A | 7/1984 | Ehnstrom |
| 4,463,575 A | 8/1984 | McCord |
| 4,522,920 A | 6/1985 | Thorsson et al. |
| 4,537,660 A | 8/1985 | McCord |
| 4,626,321 A | 12/1986 | Grethlein et al. |
| 4,746,610 A | 5/1988 | Smith |
| 4,770,748 A | 9/1988 | Cellini et al. |
| 4,801,462 A | 1/1989 | Tonna |
| 4,822,737 A | 4/1989 | Saida |
| 4,952,503 A | 8/1990 | Granstedt |
| 4,952,504 A * | 8/1990 | Pavilon ..................... 435/163 |

(Continued)

FOREIGN PATENT DOCUMENTS

EP    0039518 A    11/1981

(Continued)

*Primary Examiner* — Nathan A Bowers
*Assistant Examiner* — Gautam Prakash
(74) *Attorney, Agent, or Firm* — Price, Heneveld, Cooper, DeWitt & Litton LLP

(57) ABSTRACT

An apparatus includes a mash circulating system with pump and fermentation tank, an atmosphere circulating system with blower for circulating atmosphere between the tank and an ethanol-removal station, and an integrated refrigerating heat-transfer system with first coils for condensing out ethanol from the atmosphere, and second coils for warming the mash. A support frame supports portions of the above components, making it a transportable modular unit to facilitate installation, minimize cost, and provide for efficient operation. The entire apparatus can be up-sized or down-sized for specific applications. In one form, the system includes electrically-driven pump, blower, and refrigeration compressors, with the external energy consumption kept surprisingly low. Methods related to the above are also disclosed.

20 Claims, 4 Drawing Sheets

U.S. PATENT DOCUMENTS

| | | |
|---|---|---|
| 4,961,826 A | 10/1990 | Grethlein et al. |
| 4,994,392 A | 2/1991 | Welledits et al. |
| 5,043,284 A | 8/1991 | Welledits et al. |
| 5,124,004 A | 6/1992 | Grethlein et al. |
| 5,227,027 A | 7/1993 | Topper |
| 6,045,660 A * | 4/2000 | Savage et al. .......... 202/172 |
| 6,551,805 B2 | 4/2003 | Ho et al. |
| 6,715,404 B2 | 4/2004 | Pratt |
| 7,078,201 B2 | 7/2006 | Burmaster |
| 7,456,326 B2 | 11/2008 | Howard |
| 2004/0149137 A1 | 8/2004 | Francia |
| 2006/0191418 A1 | 8/2006 | Wasmuht et al. |
| 2008/0064075 A1 | 3/2008 | Yamamoto |
| 2009/0004713 A1 | 1/2009 | Wynn et al. |
| 2009/0006280 A1 | 1/2009 | David |

FOREIGN PATENT DOCUMENTS

| | | |
|---|---|---|
| EP | 1536016 A | 6/2005 |
| JP | 58-223496 A | 12/1983 |
| JP | 2008-182925 A | 8/2008 |
| WO | 86/05996 A | 10/1986 |

* cited by examiner

INTEGRATED APPARATUS FOR ETHANOL PRODUCTION AND EXTRACTION

BACKGROUND

The present invention relates to an integrated apparatus for ethanol production and extraction, and more particularly relates to a self-contained system useable in small, mid-level and/or large scale operations for manufacture of ethanol from organic stock, such as corn. However, the present inventive concepts are not believed to be limited to only ethanol, nor to only fermentation of a corn mash, nor to only integrated systems.

Recent energy needs (and high costs) in the United States have revived strong interest in using ethanol as a fuel source. However, many known processes focus on large sophisticated systems capable of generating large volumes of ethanol in a "factory-like" high-volume distillery. They often generate significant amounts of environmentally unfriendly "non-green" by-products (and pollutants) that must be disposed of, and further they consume large amounts of energy in order to manufacture the desired ethanol product. To the present inventors' knowledge, a system has not been developed that is highly integrated and sufficiently small to be portable and "self-contained," nor that is integrated and energy efficient in order to minimize use of external power. Further, in our opinion, to our knowledge a system has not been developed that is "mechanically simple," nor that uses known technologies in a manner so that relatively untrained "common" people and farmers can run it. Further, any such system should preferably use non-exotic technologies and not be capital-intensive, so that it is affordable for small to medium-sized entities and farms. Still further, the system should preferably be capable of providing significant amounts of ethanol concentrated sufficiently for use as combustible fuel, as well as produce useable byproducts that are not environmental pollutants, . . . and do so without the need for large amounts of external energy.

Typical ethanol extraction systems that we know of heat and/or dry mash at relatively high temperatures, and then collect ethanol after it is created by fermentation. The mash is often a ground corn mixed with water and with yeast and/or enzyme. A problem is that these systems use a lot of external energy to create ethanol. Further, they also create a lot of waste water and inconsistent by-product feed supplement. For example, in our opinion, the "spent mash" (i.e., the remaining distillers grains after fermentation has ended) from know "heat-added" processes is often inconsistent in feed quality for various livestock due to its altered (lowered) nutrient value caused by excessive heating during the distillation and distillers grains drying process. This problem is aggravated and made worse by "over-cooking" or over-heating of the mash during the fermenting process. We note that, in known apparatus and methods, high heat and over-heating often occurs in an attempt to speed up the process.

SUMMARY OF THE PRESENT INVENTION

In one aspect of the present invention, a portable integrated apparatus for producing and separating ethanol from mash includes a support frame. A mash circulating-and-fermenting system with first pipes is adapted for connection to a mash fermentation tank and a pump for pumping mash along the first pipes to a warming station having first coils. An atmosphere circulating system includes second pipes adapted for connection to the mash fermentation tank and a blower for blowing atmosphere from the mash fermentation tank to an ethanol-removing station having second coils and then back to the mash fermentation tank. A refrigerating/heat-transfer system includes lines and a compressor motivating compressible coolant fluid to flow through the first coils at the warming station and through the second coils at the ethanol-removing station. The support frame supports portions of the first and second pipes and also supports the refrigerating/heat-transfer system including the compressor, the first coils, and the second coils. In a narrower form, the frame also supports one or both of the pump and the blower. By this arrangement, a portable unit is provided facilitating installation, minimizing capital expenditure, minimizing the need for on-site design and construction, and providing efficient operation.

In another aspect of the present invention, an integrated apparatus for producing and separating ethanol from mash includes a mash circulating-and-fermenting system, an atmosphere circulating system, and a refrigerating/heat-transfer system. The mash circulating-and-fermenting system is configured and adapted to move mash from a fermentation tank past first coils in a warming station and then to move the mash back into the fermentation tank to facilitate mixing and fermentation. The atmosphere circulating system is configured to draw ethanol-laden atmosphere off of the fermentation tank, move the ethanol-laden atmosphere past second coils in an ethanol-removing station to wring out an ethanol/water mix and leave a remaining atmosphere, and move the remaining atmosphere back to the fermentation tank. The refrigerating/heat-transfer system has coolant fluid and includes the first coils arranged to use heat from the coolant fluid to warm mash in the warming station and includes the second coils arranged in the ethanol-removing station to remove heat from the ethanol-laden atmosphere as part of wringing out the ethanol/water mix.

In another aspect of the present invention, a fermentation tank and recirculation system comprises a tank for holding fermenting mash, the tank including an elevated opening and a drain, and further including at least one nozzle mounted in the elevated opening for directing mash back into the tank, a pump and pipes connecting the pump to the drain and to the at least one nozzle, and a static distributer under the at least one nozzle that is configured to spread mash dispensed into the tank by the at least one nozzle. The static distributer is configured to direct portions of the mash against a sidewall of the tank in order to accelerate mixing of the fermenting mash and evaporation of ethanol and water from the fermenting mash.

In another aspect of the present invention, a method for producing and separating ethanol from mash using modular constructions, comprises steps of providing a support frame, providing a mash circulating-and-fermenting system including first pipes and connectors adapted for connection to a mash fermentation tank and a pump, providing an atmosphere circulating system including second pipes and connectors adapted for connection to the mash fermentation tank and a blower, and providing a refrigerating/heat-transfer system with lines and a compressor for motivating compressible coolant fluid to flow through the first coils at the warming station and the second coils at the ethanol-removing station. The method further includes constructing a modular unit by supporting on the support frame portions of the first and second pipes and connectors, and also supporting on the support frame the refrigerating/heat-transfer system including the compressor, the first coils, and the second coils, moving the modular unit to an installation site, and positioning a fermentation tank adjacent the modular unit adjacent, and then connecting the portions of the first and second pipes and connectors with remaining parts of the first and second pipes and connectors to provide a functional system.

In another aspect of the present invention, a method for producing and separating ethanol from mash, comprises steps of providing an integrated system including a mash circulating-and-fermenting system, an atmosphere circulating system, and a refrigerating/heat-transfer system. The method further includes operating a pump in the circulating-and-fermenting system to move mash from a fermentation tank to a warming station with first coils and then to move the mash back into the tank to facilitate mixing and fermentation, simultaneously operating a blower in the atmosphere circulating system to draw ethanol-laden atmosphere off of the fermentation tank, and then move the ethanol-laden atmosphere past second coils in an ethanol-removing station to wring out an ethanol/water mix and leave a remaining atmosphere, and move the remaining atmosphere back to the fermentation tank, and simultaneously operating a compressor in the refrigerating/heat-transfer system to move coolant fluid from the first coils in the ethanol-removing station where heat is removed from the atmosphere as part of wringing out the ethanol/water mix to the second coils where heat is removed from the coolant fluid to warm the mash in the warming station.

In a narrower aspect, the pump, blower, and compressor all electrically driven. Further, it is contemplated that the pump, blower, and compressor can all be operated on single phase power.

In another aspect of the present invention, a method for producing and separating ethanol from mash and then further concentrating the ethanol comprises steps of providing an integrated system including a mash circulating-and-fermenting system, an atmosphere circulating system and a refrigerating/heat-transfer system, the mash circulating-and-fermenting system including a fluid tank. The method includes operating the integrated system with the fluid tank filled with fermenting mash to generate and collect a first mixture of ethanol and water, the first mixture having a first concentration of ethanol. The method further includes emptying the mash from the fluid tank, putting the first mixture into the second fluid tank, and operating the second integrated system on the first mixture to generate a second mixture of ethanol and water, the second mixture having an increased concentration of ethanol.

An object of the present invention is to provide an apparatus incorporating a refrigeration system with an ethanol generating and extraction system in a way that uses minimal external energy, yet that yields a relatively high percentage of ethanol per unit of mash, and that yields byproducts that are good food for optimal livestock production (as well as fuel-grade alcohol).

An object of the present invention is to provide a highly efficient, self-contained and portable ethanol generating and recovery system that is small enough and low cost enough for smaller farms . . . yet it can be upscaled for use in larger facilities.

These and other aspects, objects, and features of the present invention will be understood and appreciated by those skilled in the art upon studying the following specification, claims, and appended drawings.

DETAILED DESCRIPTION OF PREFERRED EMBODIMENTS

Figure 1:
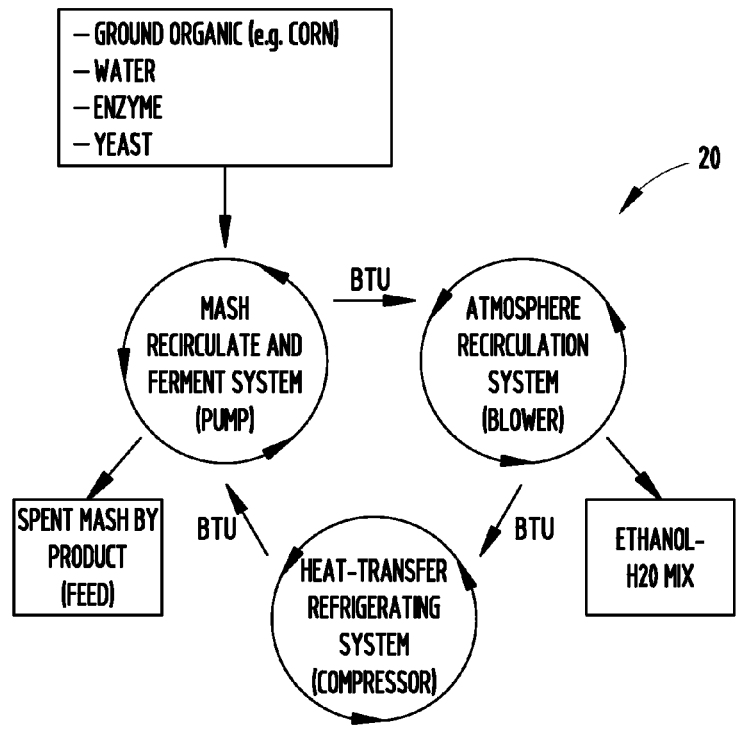
FIG. 1 is schematic drawing showing relationship of three systems in the present fermentation and ethanol extraction process, the systems including a mash-recirculating and fermentation system, a $CO_2$ atmosphere recirculation system (also called a "vapor removal system"), and a refrigerating heat-transfer system (also called a "BTU recapture system").

The present system is highly efficient, self-contained, portable, system that is small enough and low cost enough for smaller farms . . . yet it can be up-scaled for use in medium to large facilities. It incorporates and integrates a refrigerating system with its ethanol extraction system in a way that uses minimal external energy, yet that yields a relatively high percentage of ethanol per unit of mash. Further, its byproduct of spent mash (i.e. the distiller's grains product) includes a high nutrient value, since the nutrients are not destroyed by heating. Thus, the byproduct of spent mash is good food for livestock. Further, the ethanol produced is sufficiently concentrated for use as a fuel.

In the present disclosure, in areas relating to alcohol production in general, the discussion refers to "water soluble oxygenated hydrocarbons" (e.g., alcohol), because this apparatus and method will work on all alcohols. In areas relating to a process specifically producing predominantly ethanol, we use the word "ethanol." However, we are not intending this description and language to be unnecessarily limiting in the following description and/or claims.

The present system integrates and combines a mash circulating-and-fermenting system, an atmosphere circulating system (also called a "$CO_2$ atmosphere circulating system" herein), and a refrigerating/heat-transfer system. Specifically, the mash circulating-and-fermenting system moves mash from a fermentation tank to a warming station and then sprays the mash back into the tank to facilitate mixing and fermentation and evaporation/removal of additional ethanol from the fermentation tank. The atmosphere circulating system draws ethanol-laden atmosphere (also called "$CO_2$ carrier atmosphere") off of the fermentation tank, sends it past cooling coils to wring out an ethanol/water mix, and blows the remaining atmosphere back to the fermentation tank. The refrigerator/heat-transfer system includes cooling coil(s) where heat from the atmosphere is removed to separate out the ethanol/water mix from the atmosphere (i.e., the coolant fluid is heated) and second coils where heat from the coolant fluid warms re-circulating mash (i.e., the coolant fluid is cooled).

The following lists part numbers and component names:

| | |
|---|---|
| 20 | Overall system |
| 21 | alcohol/water mixture or fermenting mash liquids tank ("fermentation tank") |
| 22 | alcohol/water mixture or fermenting mash liquids (AWFML) ("fermenting mash") |
| 23 | AWFML (22) pump ("mash pump") |
| 24 | Heat Exchanger - Condenses HPRV(26D) to heat AWFML (2) liquids and condensed HPRL (26) ("mash warming station") |
| 25 | AWFML (22) Spray Nozzles ("spray nozzles with static distributer") |
| 26 | High Pressure Refrigerant Liquid (HPRL) |
| 26A | Subcooled High Pressure Refrigerant liquid uses SC (31) to cool HPRL (26) with cold $CO_2$ gas (29A) |
| 26B | Low Pressure Refrigerant Vapor/Liquid (LPRVL) uses EV (36) create LPRVL In Pipe (26B) to Cooling Coil (30) |
| 26C | Low Pressure Refrigerant Vapor (LPRV) uses Cooling Coil (30) to condense Vapors from Saturated $CO_2$ gas in Pipe (29) |
| 26D | High Pressure Refrigerant Vapor (HPRV) from Compressor (35) to condensing HXCH (24) |
| 28 | Transfer pipe from AWFML (22) in Tank (21) to Pump (23) |
| 28A | Transfer pipe from Pump (23) to HXCH (24) |
| 28B | Transfer pipe from HXCH (24) Spray nozzles (25) with AWFML (22) |
| 29 | Transfer pipe from Tank (21) headspace to Cooling Coil (30) with $CO_2$ gas Saturated with alcohol and water vapors |
| 29A | Transfer pipe from Cooling Coil (30) to Subcooling Coil (31) with cold dry $CO_2$ Gas |
| 29B | Transfer pipe from Subcooling Coil (31) to $CO_2$ blower (34) with reheated Dry $CO_2$ gas |
| 29C | Transfer pipe from $CO_2$ blower (34) to Tank (21) headspace |
| 30 | Cooling Coil uses expanding LPRVL in Pipe (26B) to condense alcohol/water Vapors from Pipe (29) ("atmosphere cooling, ethanol-removing station") |
| 31 | Subcooling Coil uses dried cold $CO_2$ gas from Pipe (29A) to subcool HPRL in Pipe (26) to Pipe (26A) ("secondary ethanol-removing station") |
| 32 | Condensed alcohol/water liquids from Cooling Coil in Pipe (30) |
| 33 | Condensed alcohol/water Tank ("ethanol collection tank") |
| 34 | $CO_2$ Blower causes $CO_2$ gas to flow through the $CO_2$ circuit |
| 35 | Refrigerant Compressor compresses LPRV (26C) into HPRV (26D) |
| 36 | Refrigerant Expansion Valve (EV) causes a pressure and temperature drop From HPRL (26A) to LPRVL (26B) |
| 37 | Diluted Alcohol/water tank |
| 38 | Diluted Alcohol/water mixture |
| 39 | Reflux Condenser Coil |
| 40 | Extended surface area fill |
| 41 | Heat Exchanger-Preheating water heat exchanger |
| 42 | Preheating/cooling process water pump |
| 43 | Preheating/cooling process water |
| 44 | Preheating/cooling process water tank |
| 45 | Alcohol/water mixture pump |
| 46 | Concentrated alcohol/water liquid |
| 47 | CAWL tank |

Figure 3:
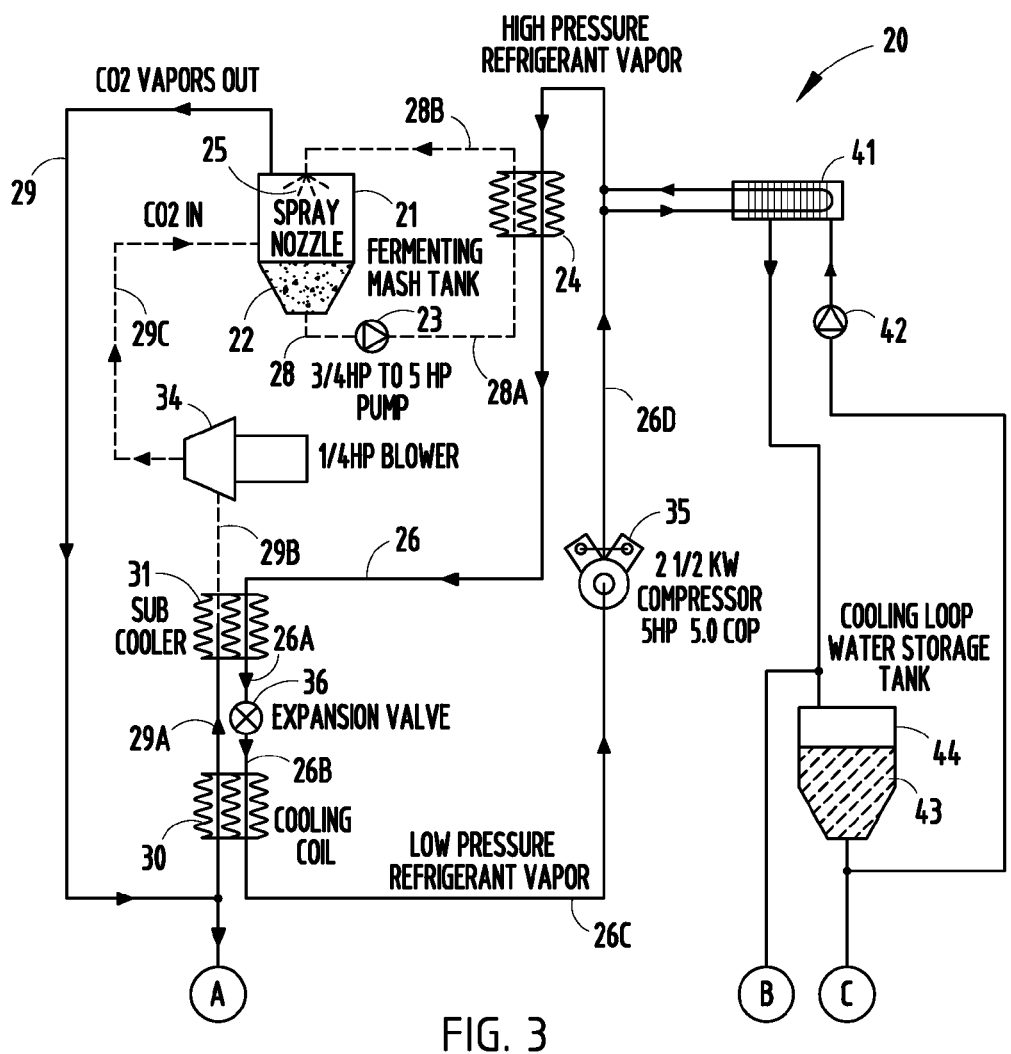
FIGS. 3 and 3A combine to form a fluid diagram showing interconnection of components, FIGS. 3 and 3A being very similar in components and arrangement, but FIG. 3 taking corn mash to generate an ethanol output of about 10%-30% ethanol, and FIG. 3A taking the output from FIG. 3 to general an ethanol output of about 90%-98% ethanol.
Figure 3A:
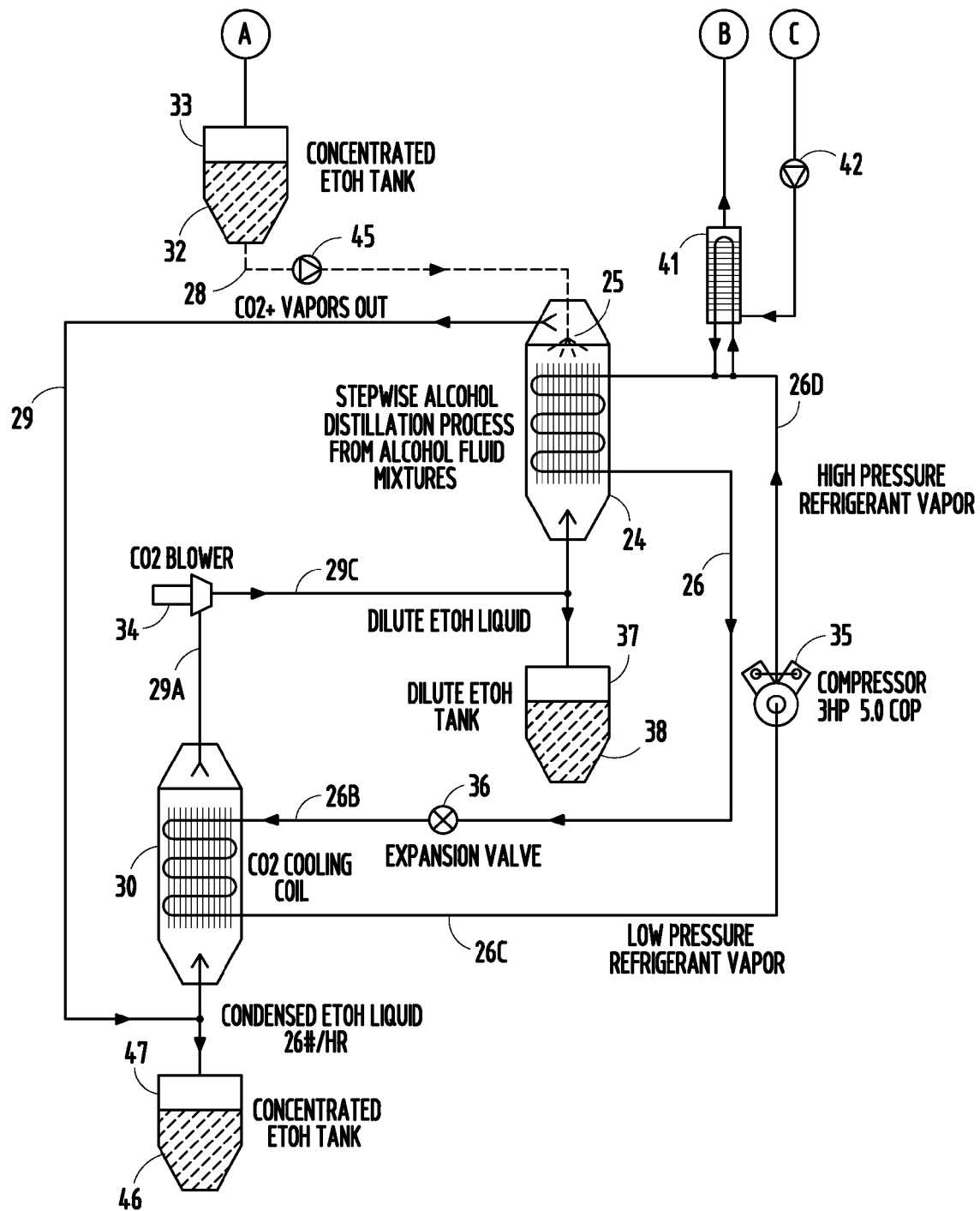

It is noted that the system shown in FIG. 3 can be used to generate an ethanol mix of about 10% to 30% ethanol, and further after cleaning, can be used a second time in a manner like that shown in FIG. 3A to purify the ethanol mix up to about 70% to 98% ethanol. For this reason, many of the same component numbers are used in both FIG. 3 and FIG. 3A. Thus, the present system is highly efficient, portable, and small enough and low cost enough for smaller farms. However, the present system is up-scalable to produce higher volumes, faster cycle times, and higher concentrations of ethanol. The present system as shown is basically a batch-type system capable of running as few as a couple days, or capable of running longer runs such as 7-10 days, as described below.

Specifically, the present system 20 includes a fermentation tank 21 with "concentrated" mash (e.g., as little as 9 gal water compared to the usual 18 gal used in existing systems per bushel of ground corn and yeast for fermentation). Mash fluid 22 is drawn off a bottom of tank 21 and pumped via pump 23 through a refrigerating coil 24. The refrigerating coil 24 takes (BTU) heat from the high pressure refrigerating vapor 26D (cooling the refrigerating vapor 26D) and puts the heat into the mash or alcohol/water fluid 22 (thus heating mash fluid 22). The heated mash fluid 22 is then sprayed back into the tank 21 via spray nozzles 25. The fermentation creates an alcohol/water mixture in fluid 22 which produces a $CO_2$/ethanol/water-vapor atmosphere in the headspace of tank 21 in proportion to the partial pressures of the alcohol, water and $CO_2$ (such as 10-55% alcohol, depending on the concentration of alcohol in the fluid 22). The headspace atmosphere from tank 21 is piped through line 29 to refrigerating coil 30 and subcooler coil 31. An ethanol-containing product 32 with relatively high ethanol content (such as 10-55%) condenses on the coil 30, and falls into the collection tank 33. Warm high pressure liquid 26 is subcooled in coil 31 by the cold $CO_2$ gas from the cooling coil 30. An expander valve is positioned between the coils 30 and 31 for allowing the high pressure refrigerant liquid 26A to expand (causing it to absorb energy) and become low pressure refrigerating vapor/liquid 26B. The refrigerating vapor 26B absorbs heat becoming low pressure refrigerating vapor 26C in coil 30 and is then communicated to compressor 34 where it is again pressurized to become high pressure refrigerating vapor 26D . . . and then is communicated to coil 24. A $CO_2$ atmosphere blower 34 draws atmosphere from coils 30 and 31 and moves it back into the headspace in tank 21. Notably, the presence of $CO_2$ in the carrier atmosphere assists the process by providing a good "clean" unreactive atmosphere for picking up the ethanol from the fermentation tank, and then for passing the ethanol-laden atmosphere through the ethanol-removal station where the atmosphere is cooled to condense out ethanol and water. The present inventors are not aware of any other system that recirculates a $CO_2$ carrier atmosphere as in the present system.

The system takes a while (such as 10 to 20 hours) for the fermentation process to reach sufficient concentrations of alcohol to start the alcohol removal system, and can operate for 4 to 12 days (or longer if mid-run feed stock additions are made, as discussed below). Once operational, the illustrated system puts out significant ethanol. Further, alcohol is carried away, such that the fermenting enzymes don't "kill" themselves in their own waste. Further, the system runs longer (up to twice as long as known systems) and generates more ethanol per unit mash (up to twice as much as compared to other known systems . . . such as 20% ethanol instead of 10% ethanol). This allows the present system 20 to run longer than other systems before it must be shut down for distiller's grains product removal (i.e., "spent mash").

It is noted that the present batch time period of operation can be extended. For example, it is contemplated that the ethanol-generating cycle can be increased by adding (once or multiple times) supplemental mash into the system. For example, by pumping a cooked starch or sugar system periodically (e.g., once daily) into the circulating fermentation tank, an operator can balance alcohol concentrations that are within the yeast tolerance levels and extraction rates of the present vapor removal system. In a simultaneous saccharification and fermentation process, one would intermittently add a ground starch feedstock (such as corn, wheat, potatoes, etc.) to maintain the proper alcohol levels for the specific yeast and enzymes. These additions could continue until the remaining solids content causes high fluid viscosity in which it is no longer practical to pump. The vapor extraction efficiency is a factor of alcohol concentration and mash temperature so that, the higher either parameter is, the more efficient the extraction. The same procedure for sugar stocks (sorghum, sugar beets, sugar cane, etc.) could be used, but without the starch to sugar converting processes.

Further, in the present system, the spent mash (also called the "distillers grains product" and also "wet distillers grains" (WDG) has excellent nutrient value (consistently better than distillers grains and solubles that have been distilled and dried at a higher temperature). In particular, the present distillers grains product has nutrients important to livestock (and with higher nutrient value), such that the present distillers grains product can be used in combination with lower value feedstock to feed livestock with higher production ratios. (In prior art known systems that use high temperature distillation/drying, the distillers grains product has a greater potential of reducing/destroying nutrient value than this present system's distillers grains . . . such that the prior art known systems product byproducts that are less effective for use as a feed for livestock, since they are unable to consistently recover good nutrients for optimal livestock production . . . noting further that nutrients are often destroyed in the prior art known systems by accidental or intentional high-heating of the mash.)

Specifically, in our experience, the spent mash byproduct created by the present system has a higher nutritional value than the byproduct of known ethanol producing system, such as 2× to 4× more nutrient value. Thus, the present spent mash byproduct is good (i.e., much better) food for livestock. A reason for this is believed to be because extraction occurs at low temperatures in the present system (i.e., 100 degrees Fahrenheit or less), versus a much higher temperature (e.g., 300-500 degrees in prior art known systems) that the mash might be exposed to in current large ethanol plants. Thus, temperature sensitive nutrients such as protein and oils in the spent mash retain more of their beneficial feeding properties with regards to livestock. Remaining wet distillers grains (WDG) in the present system may be between 11-30%+dry matter, depending on how water was used in the production process; this WDG is wet enough to be pumped and stored for extended periods in a holding tank using the excess $CO_2$ created by fermentation to blanket and preserve the WDG. The WDG would then be mixed as needed with dry feed substrate (e.g., corn stocks, straw or low quality hay/grass) to create a 50-70% moisture feed for livestock, reducing the amount of water needed by livestock to balance dry matter intake. In effect, one bushel of corn, for instance, would actually produce 78 lbs. to 100 lbs. dry matter of high quality livestock feed.

The present apparatus and system can be readily up-scaled. An enlarged system would produce a slight efficiency gain and loss of some portability. For example, a system that is capable of producing more than 20,000 gallons of alcohol per year may not be transportable on a single flat bed semi truck, whereas a system of half that annual production capability potentially could be. Down scaling the system would reverse the effects of enlarging it (stated above).

Example

Example Startup, Middle Run, Mid-Run Feed Stock Addition, and End Run

A. Start Up and Fermentation

1) Disinfect 5,000 gal tank 21, pipe 28, 28A, 28B, spray nozzles 25 and pump 23 of bacteria by filling tank 21 with 50 gallons of 10% hydrous ammonia and starting by pump 23. The hydrous ammonia raises the pH and kills undesirable bacteria.
2) Add 1,150 gal of 100 degree F. $H_2O$ to the hydrous ammonia in tank 21, using components 41-44 to provide the pre-warmed water.
3) Adjust the pH in tank 21 (monitored by PLC) to 4.3-4.2 using citrus acid or 10% NH3 solutions.
4) Mix up to 50 bushels (e.g., about 2800 lbs.) of feed stock (we used ground corn) into tank 21.
5) Repeat step 3 as necessary.
6) Add 16 oz. of yeast and 16 oz. of enzyme to tank 21 which reacts with the mash 22 in tank 21, beginning fermentation (enzyme needs to be added if the feedstock is starch based and not sugar based such as molasses). Mixing by pump 23 continues until fermentation is well underway, with the enzyme changing the feedstock starch into simple sugars, and the yeast feeding on the sugars and the resulting fermentation produces $CO_2$ and alcohol. All the while, desired temperature is maintained using components 41-44.
7) The mash created by the preceding processes is being sprayed through nozzles 25 into tank 21 by pump 23. The spraying action exposes a substantial amount of $CO_2$ vapors to the alcohol vapors which attach themselves together and both evaporate. We test the alcohol content of the mash periodically and when it reaches 3% we know the $CO_2$ vapors are saturated with alcohol vapors enough to begin our refrigerated alcohol removal and dehydration process.

B. Mid Phase: Alcohol Removal and Dehydration.
1) Start 3 hp compressor 35 and ¼ hp blower 34. Blower 34 will be controlled by a speed drive and operate at 1,750 rpm to provide 70 CFM volume of vapors being circulated through the refrigeration alcohol removal/dehydration system.
2) Blower 34 will circulate alcohol atmosphere saturated with $CO_2$ vapors from the top of tank 21 through pipe 29. The $CO_2$ vapors will be saturated with approximately 5 to 10 times the concentration of alcohol content in tank 21 mash. (For example, a 3% mash alcohol concentration will result in approximately a 15%-30% alcohol concentration in the $CO_2$ carrier atmosphere). The saturated $CO_2$ vapors enter cooling coil 30 operating at 95 degrees F. The alcohol and water vapors condense out of the $CO_2$ and drop into tank 33 at the rate of 24# per hr., leaving dry, cooled $CO_2$ vapors to return through pipes 29A, 29B and 29C to tank 21. The volume or air flow and the cooling temperature of the coils 30 and 31 are coordinated to achieve an optimal condensation and drip-off rate of condensed $ETOH/H_2O$ liquid. For example, a temperature of about 15 degrees F. for the ethanol-laden $CO_2$ atmosphere creates good extraction of ethanol from the $CO_2$ carrier atmosphere.
3) Compressor 35 creates heated high pressure refrigerant vapors (HPRV) through pipe 26D. The HPRV changes to a liquid through heat exchanger 24. Heat exchanger 24 also heats mash 22 moving via pump 23 through pipes 28A, 28B offsetting the temperature of the cool, dry $CO_2$ returning to tank 21 via blower 34 through pipe 29C. High pressure refrigerated liquid coming out of heat exchanger 24 through pipe 26 gets cooled further through sub cooler 31, enters pipe 26A and is changed to low pressure refrigerant vapor/liquid (LPRVL) through expansion valve 36. The LPRVL enters cooling coil 30 through pipe 26B and exits as low pressure refrigerated vapors through pipe 26C completing the cycle back to compressor 35.
4) Any excess heat buildup, due to heat of fermentation or compression, can be removed by using a water-temperature-control loop (i.e., components 41-44) which conserves energy by using a warm water storage tank 43/44 that will supply water for the next production cycle using reheating via a water heat exchanger.

C. Mid Run Feedstock Addition.
1) The percentage of feedstock added during start up is limited by the viscosity of mash 22 and the ability of pump 23 to move this mash. Because we are able to remove alcohol content from the mash via our $CO_2$/ethanol stripping system (i.e., the atmosphere circulating system and the mash circulating system combine to efficiently "strip" and remove alcohol from the mash), we are able to add more feedstock in the middle of the fermentation cycle. This in turn rejuvenates the fermentation cycle and gives us the ability to use less gallons of water per unit of feedstock (as little as 9 gal per bushel of ground corn in our system) for the production of food and alcohol.
2) Therefore, as the yeast starts running out of food in mash 22, the $CO_2$ produced in tank 21 starts to drop. We then add up to 50 bushels of feedstock to tank 21, which rejuvenates the fermentation process. This usually happens within 60 hours of start-up. Once again, the amount of feedstock added is limited by the viscosity of mash 22 to be such that pump 23 can move it.

D. Finish Phase.
1) As the fermentation in the tank 21 stops, the $CO_2$ produced in tank 21 drops to zero. The fermentation process is then complete. For example, this can take about 150 hrs from start up (if no mid-run feed additions are made). We contemplate that the refrigerated condensing process can continue with some benefit until mash 22 is reduced to 0.7% ethanol content (or thereabout).
2) The system is shut down and mash 22 is moved with pump 23 to a livestock feeding operation. Advantageously, the spent mash 22 will have a fat content about equal to that of the feedstock and also have a protein content of approx 35%-40%.
3) The process of yeast consuming the hydrous ammonia and the feedstock has produced 1,650 lbs dry matter of mash 22 content from 5,600 lbs of feedstock (15% moisture) (corn in our case) (i.e., about ⅓ of the original dry matter left, about ⅔ of original dry matter gone). The process has also produced 640 gal of 38% volume to volume (i.e., "v/v") ethanol to be run through our Stepwise Alcohol Distillation (STEAD) process resulting in 320 gal of 74% v/v ethanol, or, using our modified STEAD process, resulting in 253 gal of 95% v/v ethanol.

In the above example, in FIG. 3, the pump 23 has sufficient horsepower to pump mash with clumps and/or thick mash as may be encountered, such as 2-5 hp. However, under normal operating conditions, the pump need only be about 1 hp or less . . . using about 0.66 Kw. The blower 34 under normal operating conditions need only have about a ¼ hp motor. The refrigerant compressor 35 can be driven by a 3 hp motor, using about 2½ Kw and the compressor having a 5.0 COP.

System Advantages:
1) Small footprint, and portability. The present system can be made modular and as a portable/transportable single unit or few interconnectable sub-units.
2) Relatively low cost/low capital investment: The present system does not use separators (i.e. screw-type presses or centrifuges, which are expensive), nor large distillation columns (which are also expensive) or steam boilers (which is expensive, as well as potentially expensive to maintain and/or control . . . along with safety hazard issues).
3) Versatile sizing: The present system can be incrementally up-sized or down-sized for virtually any quantity of output.
4) Versatile operation: The present system can be adjusted to use a wide variety of different raw materials to form its mash.
5) Economical: The present system potentially can use one power source operating its small refrigeration equipment and pumps.
6) Practical: The present system is able to be operated on single phase power for small or isolated facilities. Further, the present system can be operated via 3 phase electrical power for larger operations . . . as well as be able to supply fuel for its own power generation in places where electrical power is not available or is obsolete.

By using corn for the mash, the present system can produce about 2.5 to 2.8 gallons of 90-95% ethanol from one bushel of corn (56 lbs. at 13% moisture). Further, it can produce byproduct spent mash having approximately 17 lbs. @ 35%-40% protein of dry matter. This spent mash can be added to and mixed with organic material normally left in a field to form 78-100 lbs. of a feed mixture well-suited for livestock (i.e., containing 13-18% protein). For example, the organic material normally left in a field does not have sufficient nutrients to merit feeding it to livestock. However, if mixed with the spent mash to form a feed mix of about 50-70% moisture, it becomes a good nutritious feed. Further, the 50/50 ethanol/water liquid collected from the fermentation extraction process can be used as a fuel (such as with diesel fumigation systems). The (external-supplied) energy input will be around 1.5 kWh per gallon (kilowatt hour per gallon) without any other (external) fossil fuel input for providing external energy into the system. 90% to 95% ethanol would require another 1 kWh per gallon, but this would be produced again without any additional (external) fossil fuel. The present system does not require boilers, steam, natural gas or any other form of combustible fuel, thus minimizing the risk of fire and/or burns from high temperature surfaces. This system's only energy (in steady state mode) is supplied by a small refrigeration system using only electricity. VOC (volatile organic compositions) emissions are substantially reduced and are condensed into the ethanol/water fuel byproduct. No organic substance or solution makes contact with a high temperature surface, nor is there any material that leaves a baked-on residue that must be scrubbed or cleaned after the distillation process is finished. (The present system operates at less than 95 degrees F.) Alcohol vapors are removed and condensed directly from the fermentation process while it is fermenting. This contrasts sharply with large ethanol generating plants, where high-temperature operations generate large VOC volumes, requiring large (and expensive) emission scrubbers and emission reducing equipment.

It is contemplated that optimal operations would pump from a cooked starch to sugar system periodically (e.g., once daily) into the circulating fermentation tank in order to better balance alcohol concentrations to within the yeast tolerance levels and for optimal extraction rates in the vapor removal system (atmosphere circulation system). In a simultaneous saccharification and fermentation process, one would intermittently add a ground starch feedstock (such as corn, wheat, potatoes, etc.) to maintain the proper alcohol levels for the specific yeast and enzymes. These additions could continue until the remaining solids content causes high fluid viscosity in which it is no longer practical to pump. The vapor extraction efficiency is a factor of alcohol concentration and mash temperature so that, the higher either parameter is, the more efficient the extraction. The same procedure for sugar stocks (sorghum, sugar beets, sugar cane, etc.) could be used, but without the starch to sugar converting processes.

FIG. 3 shows a system for collecting 10% to 55% ethanol liquid. FIG. 3A shows a second system for increasing ethanol concentration to about 50%-98%, depending on specific operating parameters. It is noted that the apparatus shown in FIG. 3 is basically repeated in FIG. 3A . . . and in fact, the system of FIG. 3 can be cleaned and re-used in place of the second system of FIG. 3A. Specifically, the present system includes a tank 33 which contains an alcohol/water fluid mixture 32 that is drawn from the bottom of tank 33 and pumped via pump 45 through spray nozzles 25 onto a refrigerant condenser coil 24. The mixture 32 is partially vaporized into the $CO_2$ stream in pipe 29C that flows counter-currently upward while mixture 32 flows downward due to gravity thus emanating as vapors a portion of the alcohol from mixture 32 into the rising $CO_2$ stream from pipe 29C. The refrigerant condenser coil 24 takes heat (BTU) from the high pressure refrigerant vapor 26D, cooling the refrigerant vapor and emitting heat into the rising $CO_2$ stream from pipe 29C and the falling alcohol/water (fluid 32). The diluted alcohol/water fluid 38 then falls into the tank 37 via gravity. The $CO_2$ stream exits the top refrigerant condenser coil 24 through pipe 29 enriched with concentrated alcohol vapors. Any excess heat buildup, due to heat of fermentation or compression, will be diverted to a water loop which will go to a warm water storage tank that will supply water for the next production cycle using a preheating water heat exchanger.

The $CO_2$ and alcohol vapors stream is transferred to refrigerant cooling coil 30 through pipe 29. The refrigerant cooling coil 30 condenses the entrained alcohol vapors from the $CO_2$ stream and the concentrated alcohol/water liquids 46 to fall into tank 47 via gravity. The remaining $CO_2$ stream is conveyed to the $CO_2$ blower (34) by pipe 29A.

Figure 4:
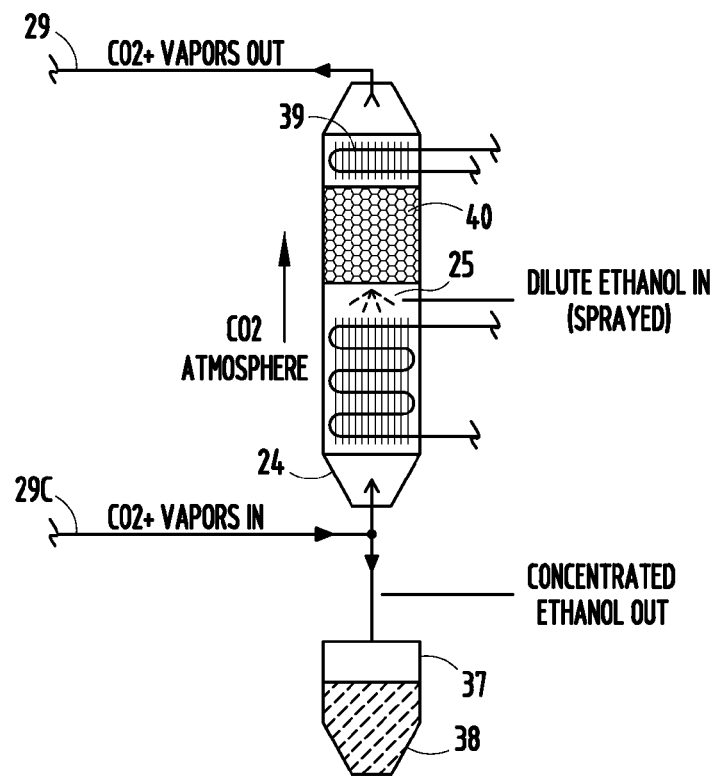
FIG. 4 is a side cross sectional view of a modified heat exchanger (24) that is not unlike the heat exchanger 24 in FIGS. 3 and 3A.

It is contemplated that a modified stepwise alcohol distillation process from alcohol fluid mixtures can be used to produce near azeotropic alcohol fluid mixtures. The apparatus of FIG. 4 raises an alcohol/water fluid concentration up to its subsequent saturated azeotropic vapor equilibrium concentration (i.e., takes 10% v/v liquid ethanol/water mixture to 95% v/v or higher). The modification uses a length of duct containing a packing material 40 to allow for sufficient surface area to ensure adequate concentration equilibrium between the liquids falling downward from the reflux condenser coil 39 located in the duct above the packing material 40 and the $CO_2$ stream containing alcohol/water vapors emanating upward from the refrigerant condenser coil 24 below. Any excess heat buildup, due to heat of fermentation or compression, will be diverted to a water loop which will go to a warm water storage tank that will supply water for the next production cycle using a preheating water heat exchanger.

There are several advantages to the present system over known systems. Focus on these items as you search. 1) The system uses a relatively low wattage motor to run the compressor 34, and there is no other external heat adding or "cooking" device in the system . . . such that energy costs are very low. 2) The absence of high heat allows the present waste to be excellent feed for livestock (especially where milk fat is important in the milk produced), making the present system much more environmentally friendly and ecological since it is not land-filled or otherwise disposed of. 3) The present system provides more ethanol per unit mash. 4) The system is simple enough and uses known technologies, such that a typical small farm can make the investment, operate it, and maintain it. 5) The present system can be made small and portable, or up-sized for larger entities and operations. 6) The present system sprays heated mash onto a static spreader as a way of accelerating evaporation of ethanol/water mix. 7) The present system combines and integrates a mash circulating system, an atmosphere circulating system, and a refrigerator/heat-transfer system.

In regards to using the word "alcohol" or "ethanol," the present apparatus and methods, the present concepts are disclosed in terms of a system generating ethanol. However, it is contemplated that the present inventive concepts are applicable to other areas where the process is talking about alcohol production in general. In the present disclosure, where we discuss alcohol production, we refer to "water soluble oxygenated hydrocarbons" because the present apparatus and process will work on all alcohols. However, in areas where we are referring to the disclosed specific process that we are now using for testing to produce predominantly ethanol, we use the word ethanol.

Figure 2:
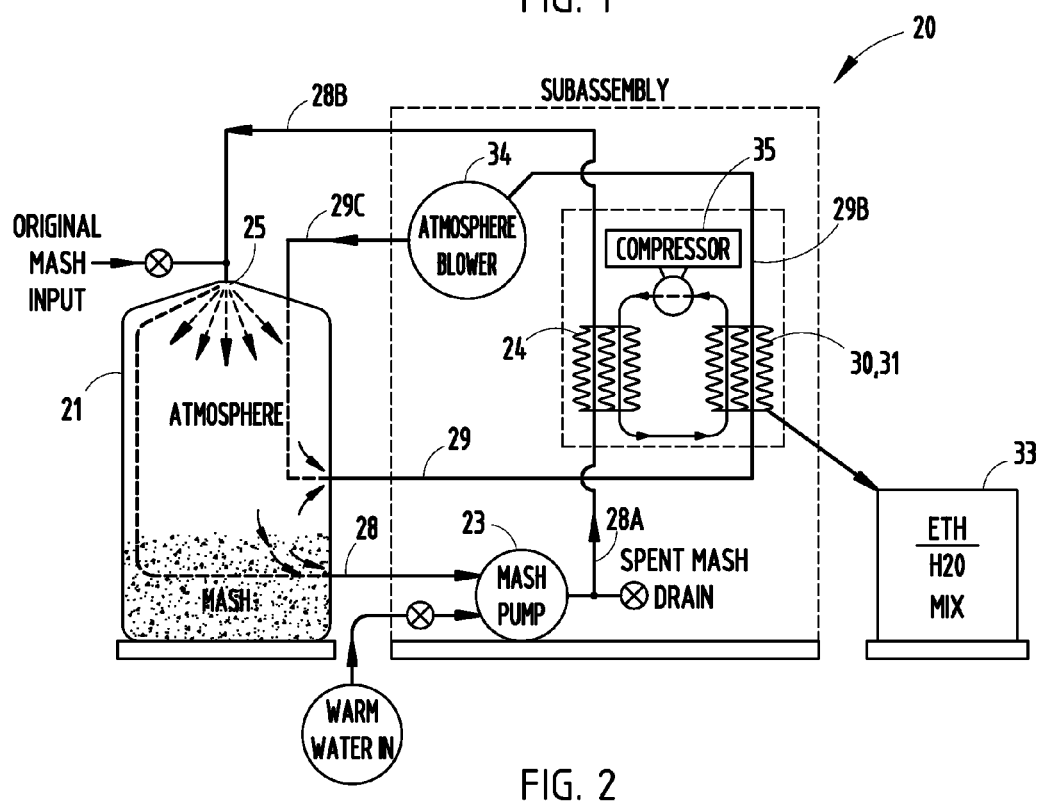
FIG. 2 is a side elevational view of a particular arrangement of components from FIG. 1, FIG. 2 including a frame and mechanical details of the particular components on the frame to form a subassembly, with the subassembly being between a mash fermentation tank and an ethanol collection tank, FIG. 2 showing a particular arrangement of those components, such that the apparatus is portable, modular, and the three "sub-systems" are well integrated.
Figure 2A:
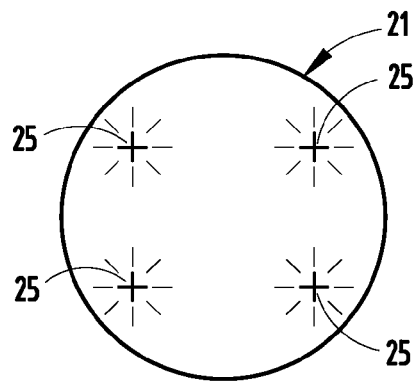
FIG. 2A is a top view of the mash fermentation tank from FIG. 2.
Figure 5:
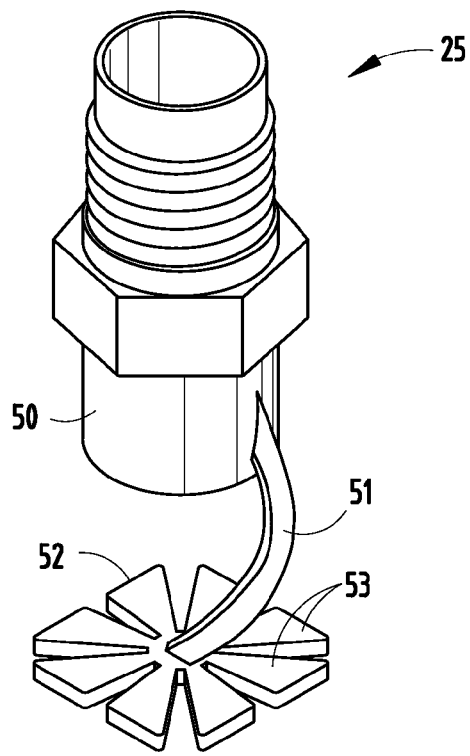
FIG. 5 is a side view of a static spray nozzle (also called a "spreader" herein).

FIG. 5 shows a static nozzle 25 (also called a spray nozzle herein). The illustrated tank 21 (FIG. 2A) has four such nozzles positioned uniformly around its top at locations a reasonable distance from the side wall of the tank 21, such as about 1-2 feet. A location of the nozzle 25 is intended to uniformly distribute mash being pumped back to the tank, so that the mash optimally spreads out at it falls to a bottom area of the tank. Further, the nozzle locations cause mash to hit and spread out on the side wall, such that the mash forms a relatively-thin mass sliding/flowing down the side wall. This further assists in evaporating ethanol into the tank's atmosphere, thus assisting in the extraction process by both agitation and also increased exposed surface area of the mash for evaporation of ethanol.

The illustrated nozzle 25 (FIG. 5) includes a pipe nipple 50 such as 1¼" diameter, with a through-hole passageway adapted to pass/flow about 30-50 gallons/minute of the mash per nozzle 25. The nozzles 25 can be attached to the top of the tank by known means, such as by a threaded portion engaging the tank or a nut on the tank. An S-shaped bent-wire arm 51 extends from the lower end of the nipple 50 to about an inch below the nipple, where it supports a horizontally-oriented distributer plate 52. The distributer plate 52 includes a center attached to the lower end of the arm 51 directly under a center of the nipple 50, and includes fan-like triangular fingers 53 extending radially, with short radial slots therebetween. By this arrangement the distributer plate 52 is configured to deflect and distribute the mash as it is pumped through the nipple 50, with the mash being deflected outward to define a non-uniform fan-shaped pattern of falling material. Optimally, nipple 50 creates/exposes substantial surface area in the falling mash. Generally stated, the more surface area the better, with the falling mash falling not as a sheet, but instead as a gently falling pattern of droplets much like a rain shower. For example, the present nozzle is not totally unlike a dispenser head on a sprinkler of an automatic sprinkler system often used in office buildings, which are designed for dropping large water drops across a floor surface, with minimal points of concentration. As noted above, a portion of the falling pattern of mash engages and runs down the side wall of the tank, thus further creating a gentle stirring action on the mash to expose and evaporate ethanol.

In one aspect of the present invention, a portable integrated apparatus for producing and separating ethanol from mash includes a support frame. A mash circulating-and-fermenting system with first pipes is adapted for connection to a mash fermentation tank and a pump for pumping mash along the first pipes to a warming station having first coils. An atmosphere circulating system includes second pipes adapted for connection to the mash fermentation tank and a blower for blowing atmosphere from the mash fermentation tank to an ethanol-removing station having second coils and then back to the mash fermentation tank. A refrigerating/heat-transfer system includes lines and a compressor motivating compressible coolant fluid to flow through the first coils at the warming station and through the second coils at the ethanol-removing station. The support frame supports portions of the first and second pipes and also supports the refrigerating/heat-transfer system including the compressor, the first coils, and the second coils. In a narrower form, the frame also supports one or both of the pump and the blower. By this arrangement, a portable unit is provided facilitating installation, minimizing capital expenditure, minimizing the need for on-site design and construction, and providing efficient operation.

To summarize, an integrated apparatus is provided for producing and separating ethanol from mash includes a mash circulating-and-fermenting system, an atmosphere circulating system, and a refrigerating/heat-transfer system. The mash circulating-and-fermenting system is configured and adapted to move mash from a fermentation tank past first coils in a warming station and then to move the mash back into the fermentation tank to facilitate mixing and fermentation. The atmosphere circulating system is configured to draw ethanol-laden atmosphere off of the fermentation tank, move the ethanol-laden atmosphere past second coils in an ethanol-removing station to wring out an ethanol/water mix and leave a remaining atmosphere, and move the remaining atmosphere back to the fermentation tank. The refrigerating/heat-transfer system has coolant fluid and includes the first coils arranged to use heat from the coolant fluid to warm mash in the warming station and includes the second coils arranged in the ethanol-removing station to remove heat from the ethanol-laden atmosphere as part of wringing out the ethanol/water mix.

Further to summarize, a fermentation tank and recirculation system includes a tank for holding fermenting mash, the tank including an elevated opening and a drain, and further including at least one nozzle mounted in the elevated opening for directing mash back into the tank. A pump and pipes connect the pump to the drain and to the at least one nozzle, and a static distributer under the at least one nozzle is configured to spread mash dispensed into the tank by the at least one nozzle. The static distributer is configured to direct portions of the mash against a sidewall of the tank in order to accelerate mixing of the fermenting mash and evaporation of ethanol and water from the fermenting mash.

Further to summarize, a method for producing and separating ethanol from mash using modular constructions, comprises steps of providing a support frame, providing a mash circulating-and-fermenting system including first pipes and connectors adapted for connection to a mash fermentation tank and a pump, providing an atmosphere circulating system including second pipes and connectors adapted for connection to the mash fermentation tank and a blower, and providing a refrigerating/heat-transfer system with lines and a compressor for motivating compressible coolant fluid to flow through the first coils at the warming station and the second coils at the ethanol-removing station. The method further includes constructing a modular unit by supporting on the support frame portions of the first and second pipes and connectors, and also supporting on the support frame the refrigerating/heat-transfer system including the compressor, the first coils, and the second coils, moving the modular unit to an installation site, and positioning a fermentation tank adjacent the modular unit adjacent, and then connecting the portions of the first and second pipes and connectors with remaining parts of the first and second pipes and connectors to provide a functional system.

Further to summarize, a method for producing and separating ethanol from mash, comprises steps of providing an integrated system including a mash circulating-and-fermenting system, an atmosphere circulating system, and a refrigerating/heat-transfer system. The method further includes operating a pump in the circulating-and-fermenting system to move mash from a fermentation tank to a warming station with first coils and then to move the mash back into the tank to facilitate mixing and fermentation, simultaneously operating a blower in the atmosphere circulating system to draw ethanol-laden atmosphere off of the fermentation tank, and then move the ethanol-laden atmosphere past second coils in an ethanol-removing station to wring out an ethanol/water mix and leave a remaining atmosphere, and move the remaining atmosphere back to the fermentation tank, and simultaneously operating a compressor in the refrigerating/heat-transfer system to move coolant fluid from the first coils in the ethanol-removing station where heat is removed from the atmosphere as part of wringing out the ethanol/water mix to the second coils where heat is removed from the coolant fluid to warm the mash in the warming station.

Notably, the pump, blower, and compressor can all be electrically driven. Further, it is contemplated that the pump, blower, and compressor can all be operated on single phase, and be relatively low horsepower ratings, such that consumption of external energy is minimized.

To summarize further, a method for producing and separating ethanol from mash and then further concentrating the ethanol comprises steps of providing an integrated system including a mash circulating-and-fermenting system, an atmosphere circulating system and a refrigerating/heat-transfer system, the mash circulating-and-fermenting system including a fluid tank. The method includes operating the integrated system with the fluid tank filled with fermenting mash to generate and collect a first mixture of ethanol and water, the first mixture having a first concentration of ethanol. The method further includes emptying the mash from the fluid tank, putting the first mixture into the second fluid tank, and operating the second integrated system on the first mixture to generate a second mixture of ethanol and water, the second mixture having an increased concentration of ethanol.

It is to be understood that variations and modifications can be made on the aforementioned structure without departing from the concepts of the present invention, and further it is to be understood that such concepts are intended to be covered by the following claims unless these claims by their language expressly state otherwise.

The embodiments of the invention in which an exclusive property or privilege is claimed are defined as follows:

1. An integrated apparatus for producing and separating ethanol from mash, comprising:
   a support frame;
   a mash circulating-and-fermenting-and-recirculating system including first pipes connecting a mash fermentation tank and a recirculation pump that pumps mash along the first pipes to a warming station having first coils and then pumps the mash back to the mash fermentation tank;
   an atmosphere circulating-and-recirculating system including second pipes connecting the mash fermentation tank and a blower blowing ethanol-water-vapor-laden atmosphere from the mash fermentation tank to an ethanol-and-water-vapor-condensing station having second coils and then blowing dried atmosphere back to the mash fermentation tank; and
   a refrigerating/heat-transfer system with lines and a compressor motivating compressible coolant fluid to flow through the first coils at the warming station and through the second coils at the ethanol-and-water-vapor-condensing station; and
   the support frame supporting portions of the first and second pipes and also supporting the refrigerating/heat-transfer system including the compressor, the first coils, and the second coils.

2. The apparatus defined in claim 1, the frame further supporting one or both of the pump and the blower.

3. The apparatus defined in claim 2, wherein the frame supports both the pump and the blower to define a portable modular subsystem.

4. The apparatus defined in claim 1, wherein the pump, blower, and compressor are electrically driven and are connected to run the apparatus without a device adding external heat.

5. The apparatus defined in claim 1, wherein the pump has a first electric motor of less than 5 hp, and the blower has a second electric motor of less than hp, and the compressor has a third electric motor of less than 3 hp.

6. The apparatus defined in claim 1, wherein the tank includes an elevated opening at a top of the tank and a drain, and further including at least one nozzle mounted in the elevated opening for directing mash back into the tank; and
   a static distributer under the at least one nozzle that is configured to spread mash dispensed into the tank by the at least one nozzle, the static distributer including a nozzle opening and a non-moving stationary distributer plate spaced below the nozzle opening that extends generally horizontally and that includes radially-extending features oriented to distribute and direct the mash flowing onto the distributer plate against a sidewall of the tank in order to accelerate mixing of the fermenting mash and evaporation of ethanol and water from the fermenting mash.

7. The system defined in claim 6, including additional openings in the tank, and wherein the at least one nozzle includes a plurality of nozzles.

8. The system defined in claim 7, wherein the openings are all in a top of the tank.

9. The system defined in claim 8, including one of the static distributers on each of the nozzles, the static distributers combining with the nozzles to cause the mash to spread into a non-uniform pattern of falling particles generally distributed across a bottom area of the tank, with at least some portion of the non-uniform pattern of mash engaging and running down sides of the tank.

10. An integrated apparatus for producing and separating ethanol from mash, comprising:
    a mash circulating-and-fermenting-and-recirculating system;
    an atmosphere circulating-and-recirculating system; and
    a refrigerating/heat-transfer system;
    the mash circulating-and-fermenting-and-recirculating system connected to and moving mash from a fermentation tank past first coils in a warming station and connected to and moving the mash back into the tank to facilitate mixing and fermentation;
    the atmosphere circulating-and-recirculating system connected to the fermentation tank and drawing ethanol-laden atmosphere off of the fermentation tank, connected to second coils and moving the ethanol-water-vapor-laden atmosphere past the second coils in an ethanol-water-vapor-condensing station to wring out an ethanol/water mix and leave a remaining atmosphere, and connected to move the remaining atmosphere back to the fermentation tank;
    the refrigerating/heat-transfer system having coolant fluid and including the first coils arranged to use heat from the coolant fluid to warm mash in the warming station and including the second coils arranged in the ethanol-removing station to remove heat from the ethanol-laden atmosphere as part of wringing out the ethanol/water mix.

11. The apparatus defined in claim 10, including a support frame supporting the refrigerating/heat-transfer system and at least parts of the mash circulating-and-fermenting-and-recirculating system and the atmosphere circulating system.

12. The apparatus defined in claim 10, wherein the mash circulating-and-fermenting-and-recirculating system includes at least one nozzle attached to the fermentation tank to drop the mash into the tank.

13. The apparatus defined in claim 12, wherein the at least one nozzle includes a plurality of spray nozzles positioned to distribute the mash in a dispersed pattern into the tank and further includes a stationary horizontal dispersion plate with radially extending features to distribute mash into the tank.

14. The apparatus defined in claim 13, wherein the nozzles each include a static distributor.

15. The apparatus defined in claim 10, wherein the mash circulating-and-fermenting-and-recirculating system includes a mash pump.

16. The apparatus defined in claim 10, wherein the atmosphere circulating-and-recirculating system includes an atmosphere blower.

17. The apparatus defined in claim 10, wherein the refrigerating/heat-transfer system includes a refrigeration compressor.

18. The apparatus defined in claim 10, including an ethanol-water collection tank for accepting the ethanol/water mix from the ethanol-water-vapor-condensing station.

19. The apparatus defined in claim 10, including a cooling loop operably connected to the mash circulating-and-fermenting-and-recirculating system for stabilizing and controlling a temperature of the mash in the fermentation tank.

20. The apparatus defined in claim 10, wherein the refrigerating/heat-transfer system, the mash circulating-and-fermenting-and-recirculating system, and the atmosphere circulating-and-recirculating system are electrically driven by motors having a total horsepower of about 7½ horsepower.

* * * * *

UNITED STATES PATENT AND TRADEMARK OFFICE
CERTIFICATE OF CORRECTION

| | | |
|---|---|---|
| PATENT NO. | : 7,972,825 B2 | Page 1 of 1 |
| APPLICATION NO. | : 12/370721 | |
| DATED | : July 5, 2011 | |
| INVENTOR(S) | : Scott Sovereign et al. | |

It is certified that error appears in the above-identified patent and that said Letters Patent is hereby corrected as shown below:

Column 15
Claim 5, line 56, "less than hp" should be -- less than ½ hp --.

Signed and Sealed this

Thirteenth Day of September, 2011

David J. Kappos
*Director of the United States Patent and Trademark Office*